United States Patent
Kuzma et al.

(10) Patent No.: US 6,889,094 B1
(45) Date of Patent: May 3, 2005

(54) ELECTRODE ARRAY FOR HYBRID COCHLEAR STIMULATOR

(75) Inventors: Janusz A. Kuzma, Parker, CO (US); William Vanbrooks Harrison, Valencia, CA (US); Thomas J. Balkany, Coral Gables, FL (US)

(73) Assignee: Advanced Bionics Corporation, Slymar, CA (US)

( * ) Notice: Subject to any disclaimer, the term of this patent is extended or adjusted under 35 U.S.C. 154(b) by 0 days.

(21) Appl. No.: 09/979,800

(22) PCT Filed: May 12, 2000

(86) PCT No.: PCT/US00/13121
§ 371 (c)(1),
(2), (4) Date: Nov. 13, 2001

(87) PCT Pub. No.: WO00/69513
PCT Pub. Date: Nov. 23, 2000

Related U.S. Application Data
(60) Provisional application No. 60/135,217, filed on May 21, 1999, and provisional application No. 60/134,290, filed on May 14, 1999.

(51) Int. Cl.[7] ............................................. A61N 1/05
(52) U.S. Cl. ..................................................... 607/137
(58) Field of Search .................................... 607/57, 137

(56) References Cited

U.S. PATENT DOCUMENTS

| | | | |
|---|---|---|---|
| 4,809,712 A | 3/1989 | Kuzma | 128/784 |
| 6,074,422 A | 6/2000 | Berrang et al. | 623/10 |

Primary Examiner—Jeffrey R. Jastrzab

(74) Attorney, Agent, or Firm—Bryant R. Gold

(57) ABSTRACT

A cochlear electrode array is adapted for implantation within the basal end of the scala tympani duct of a human cochlea. A first embodiment of the cochlear electrode array (10) comprises a skinny, elongate carrier (12) of from 6–8 mm in length. Four to eight spaced-apart electrode contacts (14) reside along one of the flat sides of the carrier, each of which is connected to a respective wire (22) embedded within the carrier. The wires exit a proximal end of the carrier via a wire bundle. The wire bundle, in turn, is connectable to an implantable cochlear stimulator (ICS) or equivalent pulse generator. The electrode array (10) is inserted into the relatively straight portion of the basal end of the scala tympani duct of the cochlea through a small slit (42) made in the round window membrane that separates the cochlea from the middle ear. The slit is oriented so as to place the electrode contacts facing the modiolar wall (32). The proximal end of the carrier may include flexible flaps (16) or tines that maintain the electrode array in its desired position within the basal end of the cochlea. Such tines or flaps further help seal the carrier against the slit opening to present fluids from escaping the cochlea. The cochlea thus remains filled with fluid which can activate hair cells as fluid waves are established through motion of the round window membrane. In use, electrical stimulation is provided only to the basal end of the cochlea through the electrode array to supplement hearing of high frequency sounds. Normal hearing (activation of hair cells through fluid motion) occurs at the apex and middle regions of the cochlea for sensing lower frequency sounds. A second embodiment of the cochlear electrode (100) is made by forming a small (120) of about 0.4 mm diameter on the end of a very fine flexible platinum/iridium (Pt/Ir) wire (140). At a proximal end of the wire, a suitable connector (540) allows the wire to be detachably connected to a pulse generator (500).

9 Claims, 6 Drawing Sheets

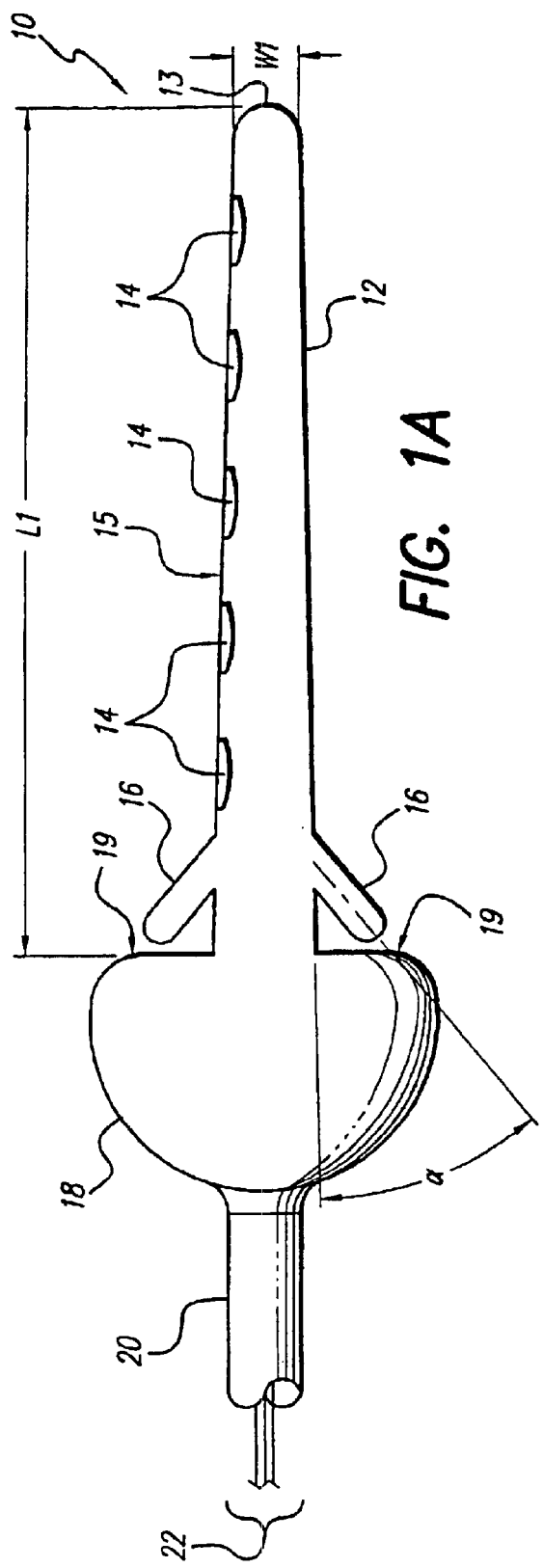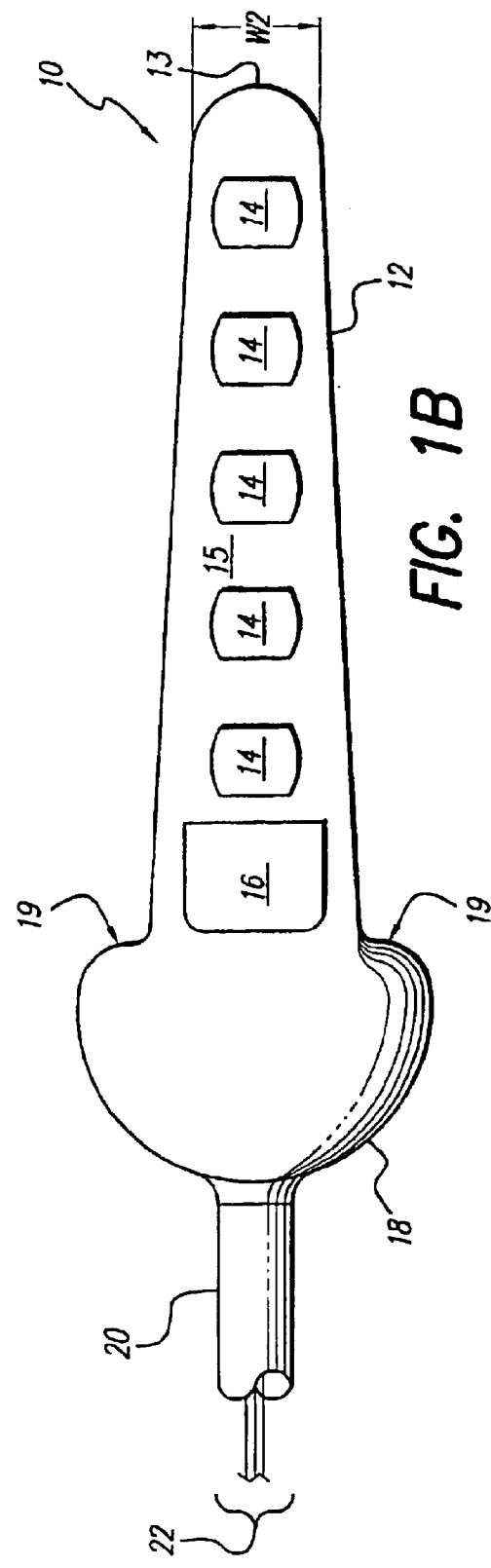

ELECTRODE ARRAY FOR HYBRID COCHLEAR STIMULATOR

This application is a 371 of PCT/US00/13121 May 12, 1999, which claims benefit of 60/134,290 May 14, 1999 and of 60/135,217 May 21, 1999.

BACKGROUND OF THE INVENTION

The present invention relates to implantable electrode arrays, and more particularly to an implantable electrode array configured for implantation within the basal end of the scala tympani duct of a human cochlea. Such electrode array is best suited for use with a hybrid cochlear stimulation of the type described in applicant's copending patent application, filed concurrently herewith, entitled "Hybrid Implantable Cochlear Stimulation Hearing Aid System" Ser. No. PCT/US00/13122 which application is incorporated herein by reference. A hybrid cochlear stimulation system provides electrical stimulation only to the basal end of the cochlea to stimulate ganglion cells responsible for sensing higher-frequency sounds, and relies on normal hearing (activation of hair cells through fluid motion within the cochlea), which may occur with or without the assistance of a conventional or a custom hearing aid, to sense middle-to-lower frequency sounds.

Hearing loss is generally of two types: conductive and sensorineural. Of these, conductive hearing loss occurs where the normal mechanical pathways for sound to reach the hair cells in the cochlea are impeded, for example, by damage to the ossicles. Conductive hearing loss may often be helped by use of conventional hearing aids, which amplify sound so that acoustic information does reach the cochlea and the hair cells. Some types of conductive hearing loss are also amenable to alleviation by surgical procedures.

Sensorineural hearing loss, on the other hand, results due to the absence or the destruction of the hair cells in the cochlea which are needed to transduce acoustic signals into auditory nerve impulses. Persons who suffer from sensorineural hearing loss are unable to derive any benefit from conventional hearing aid systems, no matter how loud the acoustic stimulus is made, because their mechanisms for transducing sound energy into auditory nerve impulses have been damaged. Thus, in the absence of properly functioning hair cells, there is no way auditory nerve impulses can be generated directly from sounds.

To overcome sensorineural deafness, there have been developed numerous cochlear implant systems—or cochlear prosthesis—which seek to bypass the hair cells in the cochlea by presenting electrical stimuli directly to the ganglia of the auditory nerve located adjacent the modiolar wall of the cochlea. When triggered, the ganglia, also referred to as ganglion cells send nerve impulses to the brain via the auditory nerve, leading to the perception of sound in the brain, and an at least partial restoration of hearing function. The common denominator in these cochlear prosthesis systems has been the implantation into the cochlea of electrodes which are responsive to a suitable external source of electrical stimuli and which are intended to transmit those stimuli to the ganglion cells, and thereby to the auditory nerve fibers.

It is estimated that a large segment of the hearing-impaired population exhibit sensorineural hearing loss relative to high frequency sounds, but maintain the ability to transduce middle-to-lower frequency sounds through functioning hair cells. For this segment of the population, there is thus a need for a "hybrid" cochlear stimulation system that electrically stimulates only the ganglion cells responsible for sensing higher frequency sounds, while allowing the normal hearing process to function for the purpose of sensing lower frequency sounds.

A cochlear prosthesis operates by direct electrical stimulation of the auditory nerve cells, bypassing the defective cochlear hair cells that normally transduce acoustic energy into electrical activity in such nerve cells. Because the ganglion cells responsible for sensing higher frequency sounds are all generally located in or near the basal end of the cochlea (the end of the cochlea nearest the round window membrane), a hybrid cochlear stimulation system thus requires an electrode array that can be inserted within the cochlea a sufficient depth to be near such cells, but which also does not block or significantly interfere with the normal functioning of the cochlea for hair cells located deeper within the cochlea. No such electrode array, to applicants' knowledge, currently exists.

SUMMARY OF THE INVENTION

The present invention addresses the above and other needs by providing a cochlear electrode array suitable for use with a hybrid cochlear stimulation system. In one embodiment, the cochlear electrode array comprises a relatively skinny, elongate carrier of from 6–8 mm in length. Four to eight spaced-apart electrode contacts reside along one of the flat sides of the carrier, each of which is connected to a respective wire embedded within the carrier. The wires exit a proximal end of the carrier via a wire bundle. The wire bundle, in turn, is connectable to an implantable cochlear stimulator (ICS) or equivalent pulse generator. The electrode array is inserted into the relatively straight portion of the basal end of the scala tympani duct of the cochlea through a small slit made in the round window membrane that separates the cochlea from the middle ear. The slit is oriented so as to place the electrode contacts facing the modiolar wall. The proximal end of the carrier may include flexible flaps or tines that maintain the electrode array in its desired position within the basal end of the cochlea. Such tines or flaps further help seal the carrier against the slit opening to prevent fluids from escaping the cochlea. The cochlea thus remains filled with fluid which can activate hair cells as fluid waves are established through motion of the round window membrane, which is the normal process for hearing.

In use, electrical stimulation is provided only to the basal end of the cochlea through the electrode array to supplement hearing of high frequency sounds. Normal hearing processes (activation of hair cells through fluid motion) occur at the apex and middle regions of the cochlea for sensing lower frequency sounds. As needed, such normal hearing processes may be supplemented by conventional or custom hearing aid apparatus, including in-the-ear-canal or middle-ear hearing aid devices.

In another embodiment, a cochlear electrode is provided that is made by forming a small ball electrode of about 0.4 mm diameter on the end of a very fine, or thin, flexible platinum/iridium (Pt/Ir) wire. The fine Pt/Ir wire is insulated at every point along its length, except at its ends. At a distal end of the wire, the ball electrode is formed. At a proximal end of the wire, a suitable connector allows the wire to be detachably connected to a pulse generator or other stimulator or electrical circuitry. The insulation is made from a suitable biocompatible insulative coating, such as a Teflon® coating. The electrode thus formed at the distal end of the wire is referred to hereafter as a "ball electrode".

To insert the ball electrode into the cochlea, a very small incision or slit, e.g., not much longer than the diameter of the ball electrode, is first made in the membrane of the round window. The ball electrode is then loaded into the distal tip of an insertion tube in such a way that the ball end is held at the distal tip of the tube by tension applied to the thin wire. The end of the insertion tube is preferably beveled so as to better hold the electrode ball in position at its distal tip.

Insertion of the ball electrode into the cochlea is made by forcing the ball electrode, held at the distal end of the insertion tube, through the small slit made in the round window membrane. Advantageously, as needed, the round window tissue will stretch to allow the ball electrode to pop through to the inner side of the cochlea. Once thus inserted into the inner side of the cochlea, the round window membrane closes tightly around the thin, flexible wire, thereby holding the ball electrode in place on the inside of the membrane, while minimizing any leak of fluid from the cochlea.

Once the ball electrode has been thus inserted into the cochlea through the small slit in the round window membrane, the insertion tube may be withdrawn, leaving behind the ball electrode held against the inside of the round window membrane with the thin flexible lead extending through the tiny incision made in the round window membrane. The thin wire may then be coiled within the inner ear cavity, or elsewhere, as required to adjust its length, and connected to a suitable electrical stimulator through an appropriate connector. The electrical stimulator may then be controlled in an appropriate manner so as to provide electrical current stimulation through the ball electrode to the tissue at the basal end of the cochlea, to thereby compensate for high frequency hearing loss, and/or to suppress tinnitus. A reference or return electrode, e.g., located on the case of the stimulator, may be used with the ball electrode in order to provide a suitable electrical return path for the electrical current that is applied through the ball electrode.

It is thus a feature of the present invention to provide an electrode array that may be inserted into the basal end of the cochlea of a hearing-impaired patient so that ganglion cells located near the basal end of the cochlea may be stimulated directly with electrical stimuli, thereby enhancing the ability of the patient to sense high frequency sounds.

It is a further feature of the invention to provide an electrode array suitable for insertion into the basal end of the scala tympani duct of a human cochlea without destroying the function of the round window membrane, and without causing fluid to escape from the scala tympani duct, thereby allowing normal hearing processes (fluid motion activation of hair cells) to occur in regions other than the basal end of the cochlea.

It is another feature of the invention, in accordance with one embodiment thereof, to provide a small ball electrode that may be inserted into the basal end of the cochlea through a minimally invasive insertion process. Such electrode may thereafter be used to stimulate ganglion cells located near the basal end of the cochlea for the purpose of, e.g., compensating for high frequency hearing loss and/or to suppress tinnitus.

It is yet an additional feature of the invention, in accordance with one embodiment, to provide a method of implanting a ball electrode through the round window membrane of the cochlea that is minimally invasive, thereby avoiding, or at least significantly minimizing, any adverse reaction to the implant, such as tissue formation or new bone formation that adversely affects residual hearing function in the implanted ear.

BRIEF DESCRIPTION OF THE DRAWINGS

The above and other aspects, features and advantages of the present invention will be more apparent from the following more particular description thereof, presented in conjunction with the following drawings wherein:

FIG. 1A is a side view of an electrode array made in accordance with a first embodiment the present invention;

FIG. 1B is a medial side view of the electrode array of FIG. 1A;

Corresponding reference characters indicate corresponding components or elements throughout the several views of the drawings.

DETAILED DESCRIPTION OF THE INVENTION

Figure 2:
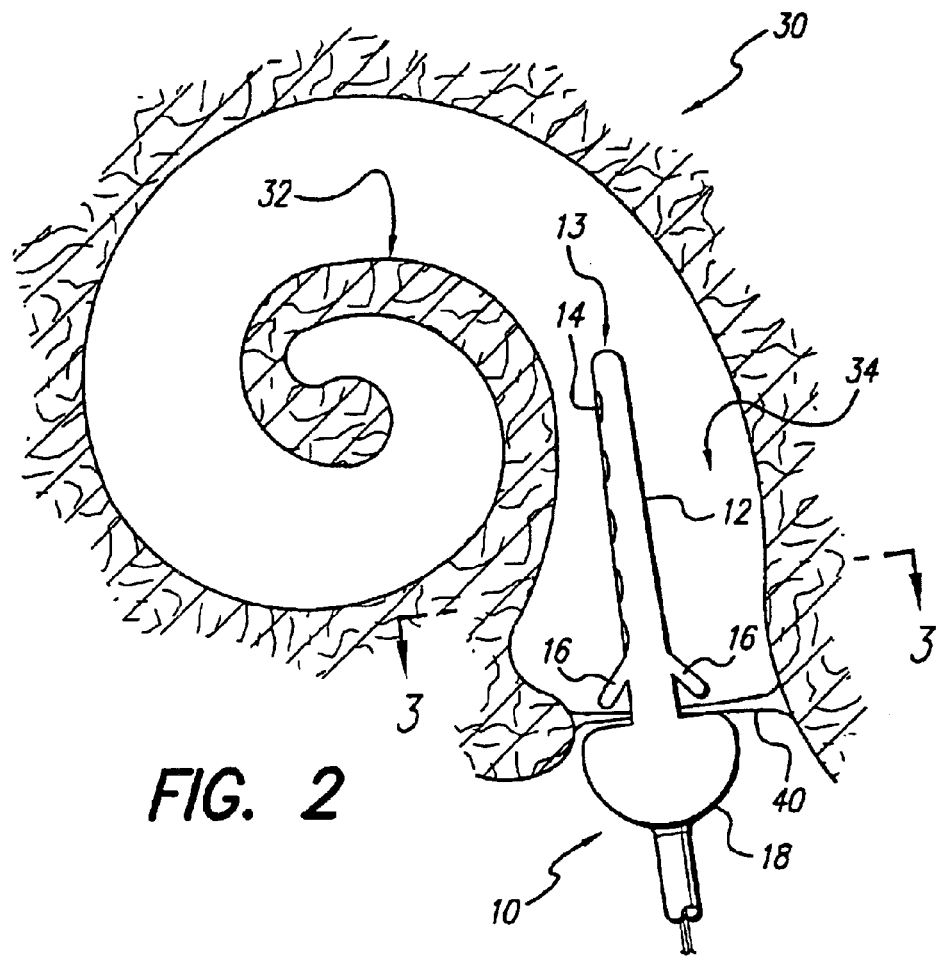
FIG. 2 illustrates placement of the electrode array of FIGS. 1A and 1B into the basal end of the scala tympani duct of a human cochlea in accordance with the present invention.

The following description is of the best mode presently contemplated for carrying out the invention. This description is not to be taken in a limiting sense, but is made merely for the purpose of describing the general principles of the invention. The scope of the invention should be determined with reference to the claims.

An electrode array 10 made in accordance with a first embodiment of the present invention is illustrated in FIGS. 1A and 1B. FIG. 1A is a side view of the electrode array 10; and FIG. 1B is a view of a medial side of the electrode array 10. (Thus, for purposes of the present application, the "medial side" of the electrode array 10 is the side on which a plurality of spaced-apart electrode contacts 14 are located.)

As seen in FIGS. 1A and 1B, the electrode array 10 includes a plurality of spaced-apart electrode contacts 14 on a flexible carrier 12. In the preferred embodiment, each of the electrode contacts 14 resides on the same side the medial side 15—of the carrier 12. Each electrode contact 12 has at least one wire conductor 22 connected thereto. These wire conductors are embedded within the flexible carrier 12 and exit through a proximal end of the carrier 12 within a flexible cable 20. The cable 20, including its wire conductors 22, connect to a pulse generator, or other suitable stimulator (not shown). Such wire conductors 22 thus provide a means for making electrical contact with each of the electrode contacts 14. When used as part of a hybrid or other cochlear stimulator system, the pulse generator, or other stimulator, thus generates electrical pulses or electrical currents ("electrical stimuli") that is/are applied to selective ones of the electrode contacts 14 in order to evoke a desired response from the ganglion cells located in the vicinity of the electrode contacts 14.

At a proximal end of the electrode array 10 is a head 18. The head 18 comprises a portion of the flexible carrier 12 that is larger than the carrier 12, thereby creating a shoulder 19 that defines the boundary between the carrier 12 and the head 18. A plurality of flaps 16, or tines, protrude out from the body of the carrier 12 near the proximal end of the carrier at a slanting angle α, where α is as defined in FIG. 1A. Typically α is an acute angle of from 20–45°. The wire conductors 22 pass through the head 18, exiting via the cable 20 which is connected to the head 18 at its proximal end.

The electrode array 10 is thinner in one direction than in the other. Stated differently, the electrode array 10 is flattened in one direction, and when viewed in cross section (see FIG. 3), resembles a pancake or paddle. As seen in FIG. 1A, for example, with the electrode contacts 14 facing upwards, the width of the carrier body 14 is W1. As seen in FIG. 1B, with the electrode contacts 14 facing out of the plane of the paper, the width of the carrier body 14 is W2, where W2 is 3–4 times larger than W1. Typically, W1 may be about 0.5 to 1.0 mm; whereas W2 may be on the order of 2–3 mm.

The length of the electrode array 10, from the shoulder 19 to a distal tip 13 is a distance L1. This distance L1 will typically be 6–8 mm. The number of spaced-apart electrode contacts 14 positioned on the medial side of the carrier body 14 may vary from four to eight.

As seen in FIGS. 1A and 1B, the electrode contacts 14 are all on a medial side of the electrode array, i.e., are all on the same side of the carrier 12, and the medial side is one of the "flat" sides of the carrier 12. Such positioning is preferred because when inserted into the cochlea, this medial side of the electrode array 10 is positioned so as to face the modiolar wall of the cochlea, where the ganglion cells are located. Thus, such positioning places the electrode contacts closer to the modiolar wall, and thereby allows electrical stimulation of the ganglion cells to occur more efficiently (i.e., with less power). However, it should be noted that such positioning of the electrode contacts 14 is not mandatory. In practice, the electrode contacts 14 could be located on any side of the flexible carrier body 14, or on all sides (e.g., bands or rings), and the electrode array could still perform its intended function of stimulating the ganglion cells located near the basal end of the cochlea.

Turning next to FIG. 2, a preferred way of inserting an electrode array made in accordance with the first embodiment of the invention into a cochlea 30 is illustrated. As described previously, the electrode array 10 is a short electrode array, e.g., 6–8 mm, compared with a conventional cochlear electrode array, (which is typically 25–30 mm in length). Thus, the electrode array 10 extends into the scala tympani duct only in the region 34 near the basal end of the scala tympani duct, and the array 10 remains substantially straight, without having to extend past the first bend of the spiraling scala tympani duct.

Figure 4:
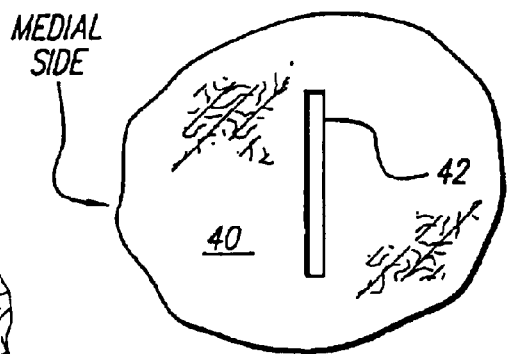
FIG. 4 depicts the manner in which a slit is made in the round window membrane in order to allow the electrode array to be inserted into the cochlea.

As seen in FIG. 2, the electrode array 10 may be inserted into the basal region 14 through a narrow slit 42 (FIG. 4) made in the round window membrane (round window) 40. The electrode array 10 is inserted through the slit 42 until the flaps or tines 16 have passed through the slit into the basal region 34, and the shoulder 19, formed by the head 18, rests against the middle-ear side of the round window membrane 40. Through this type of insertion, the body 12 of the electrode array 12 effectively plugs the narrow slit 42 so that the fluid normally present within the scala tympani duct is retained therein. Retaining such fluid within the scala tympani duct is important so that the normal hearing processes may continue throughout the remaining portions—e.g., the middle and apex portions—of the cochlea. Further, the flexible flaps or tines 16, once passed through the slit 42, prevent the electrode array from slipping out of the slit 42.

Figure 3:
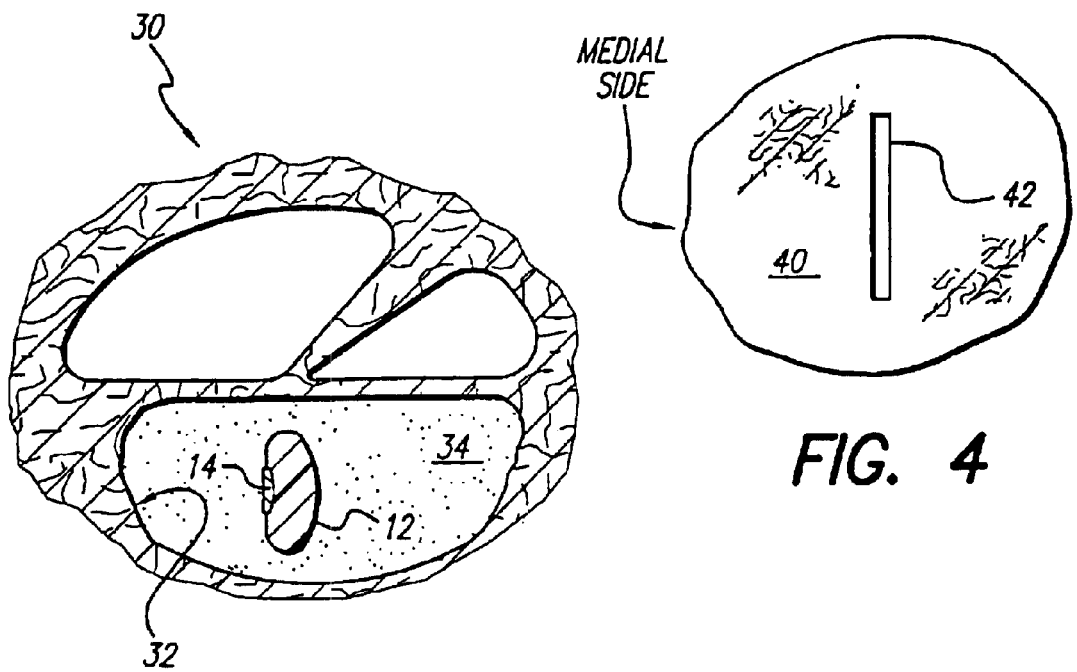
FIG. 3 is a sectional view of the cochlea taken along the line 3—3 of FIG. 2.

Thus, it is seen that the array 10 is held in position within the basal region 34 by the shoulder 19, and flaps or tines 16. Moreover, because the electrode array 10 is "flattened", or pancake shaped (when viewed in cross section as seen in FIG. 3), the distal tip 13 and the rest of the array 10 readily slide through the slit 42. The slit 42 advantageously maintains the medial side of the array 10 facing in the right direction—i.e., facing the modiolar wall 32. Insertion of the electrode array 10 into the cochlea is thus a simple and straightforward process, requiring only a few seconds, once access to the round window has been obtained.

The electrode array 10 may be made using conventional techniques, from conventional materials, as is known in the cochlear electrode array art. One approach for making a cochlear electrode array with all of the electrode contacts on the medial side is described in U.S. patent application Ser. No. 09/216,063, filed Feb 9, 1999, which application is incorporated herein by reference. The only changes needed to make the electrode array 10 described herein from the array described in the referenced patent application are relatively simply design changes relating to the size and shape of the mold and die which are used. Those of skill in the electrode art could readily make such modifications without difficulty.

Figure 5:
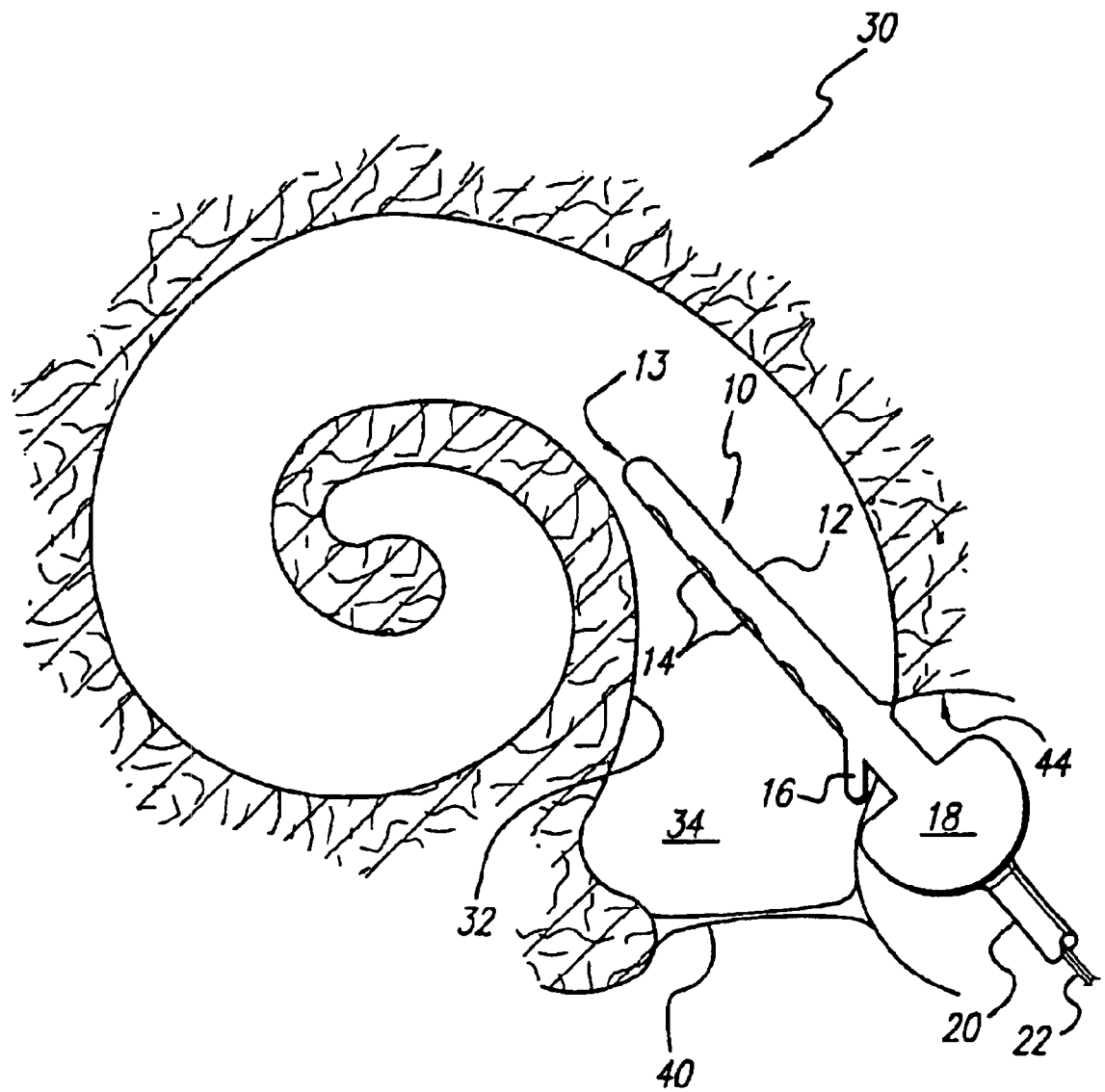
FIG. 5 shows an alternate insertion technique of the electrode array of FIGS. 1A and 1B into the cochlea.

Turning next to FIG. 5, an alternate method of inserting the electrode array 10 into the basal region 34 of the scala tympani duct is illustrated. This alternate method involves leaving the round window membrane 40 intact without making a slit therein, and without having the head 18 of the electrode 10 placed against it. This allows the round window membrane to more effectively perform its intended function during normal hearing of vibrating in response to sensed acoustic waves, and setting up fluid waves within the fluid held within the scala tympani duct, which fluid waves may then activate the hair cells in the middle and apical regions of the cochlea. The alternate approach shown in FIG. 5 has the electrode array 10 being inserted into the basal region 34 through a side slit made near the round window membrane. Such side slit is made at the bottom of a cavity 44, which cavity 44 is made in the bone structure adjacent the cochlea 30. Once made, the electrode array 10 slides through the slit as shown, and is held in position by the shoulder 19 and flaps or tines 16, with its medial side and the electrode contacts 14 facing the modiolar wall 32.

As described above, it is thus seen that the present invention provides an electrode array that may be easily inserted into the basal end of the cochlea of a hearing-impaired patent, with its electrode contacts held in position facing the modiolar wall where the ganglion cells responsible for sensing higher frequency sounds are located.

It is further seen that the electrode array 10 of the invention may be inserted into the basal end of the scala tympani duct of a human cochlea without destroying the function of the round window membrane, and without leaving an open hole through which fluid may escape from the scala tympani duct. This advantageously allows normal hearing processes (fluid motion activation of hair cells) to occur in regions other than the basal end of the cochlea.

As described above, it is also seen that the electrode array 10 described herein may be used with a hybrid cochlear implantable stimulator system designed to provide electrical stimulation through the electrode array for sensing high frequency audio sounds, which allows normal hearing processes to occur for sensing low and middle frequency sounds. Such a hybrid cochlear stimulation system is described in applicants' copending patent application, filed concurrently herewith, entitled "Hybrid Implantable Cochlear Stimulation Hearing Aid System"Ser. No. PCT/US00/13122.

Figure 6:
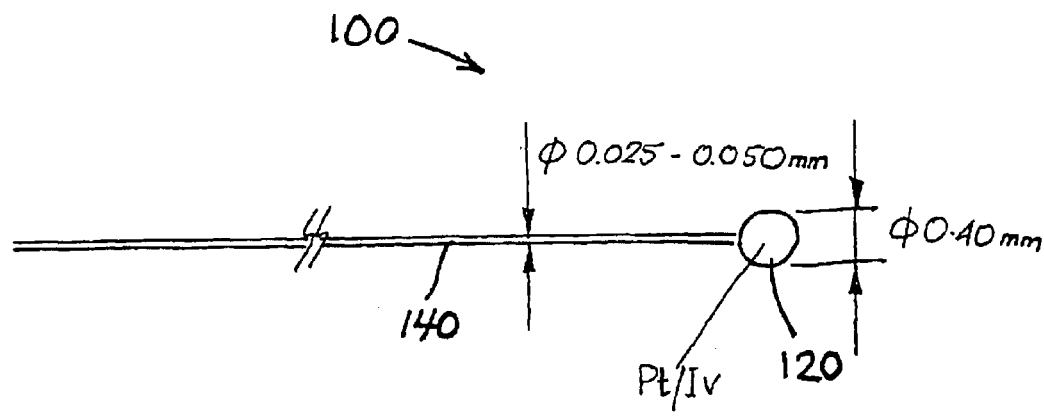
FIG. 6 shows a ball electrode in accordance with a second embodiment of the present invention attached to the distal end of a thin, flexible, insulated Pt/Ir wire.

Turning next to FIG. 6, there is shown an electrode 100 made in accordance with a second embodiment of the invention. The electrode 100 includes an exposed (non-insulated) ball electrode 120 located at the distal end of a flexible wire 140. The ball electrode 120 is made from a suitable biocompatible conductive material, such as Pt/Ir, and has a diameter of about 0.40 mm. The wire 140 comprises a thin, e.g., 0.025 to 0.050 mm diameter, flexible Pt/Ir wire, insulated with a suitable biocompatible material, such as Teflon® insulation. The ball electrode 120 may be formed using any suitable process, e.g., flaming and forming the end of the wire 140 into a ball of the desired size.

Figure 7:
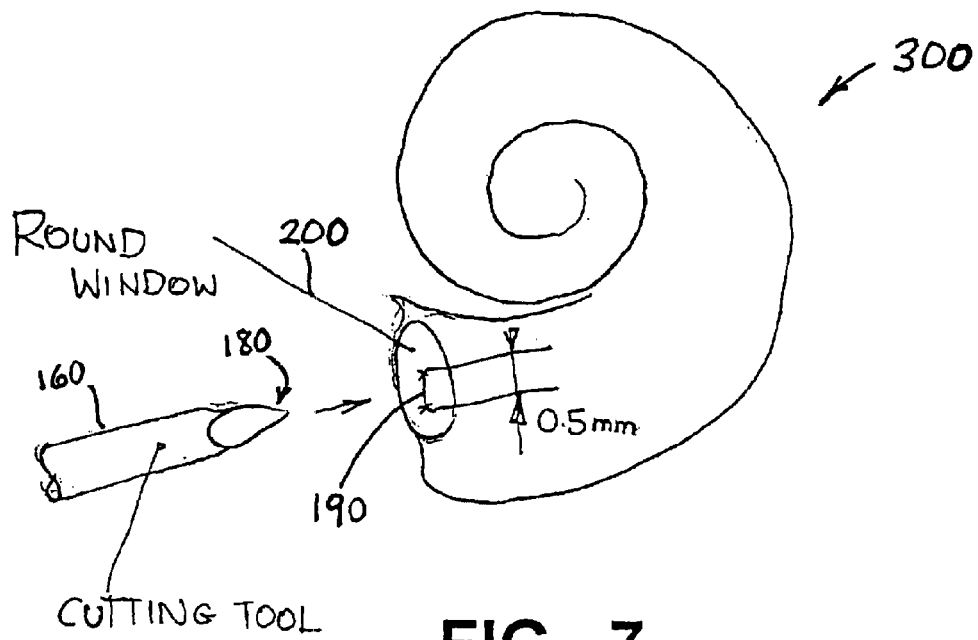
FIG. 7 illustrates the first step of implanting the ball electrode, i.e, making a small incision or slit in the round window membrane with a sharp cutting tool.

FIG. 7 illustrates the first step of implanting the ball electrode 100. This first step involves making a small incision or slit 190 in the round window membrane 200 of the cochlea 300. The slit 190 should have a length that is at least as large as the diameter of the ball electrode, and preferably a little larger. For example, where the ball electrode 120 has a diameter of 0.40 mm, the slit 190 could have a length of about 0.50 mm. The small incision or slit 190 may be made in the round window membrane 200 using any suitable technique, e.g., by cutting the membrane 200 with the sharp tip 180 of a cutting tool 160.

Figure 8A:
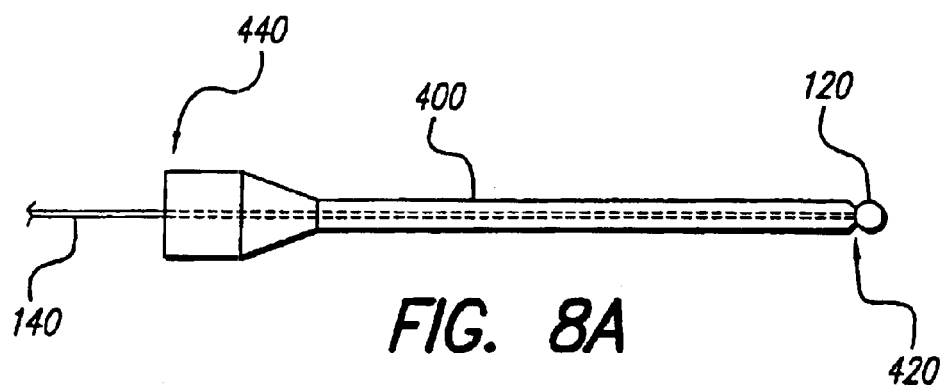
FIG. 8A depicts the ball electrode loaded under tension at the distal end of an insertion tube.
Figure 8B:
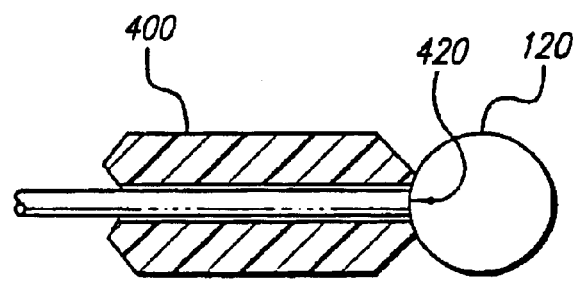
FIG. 8B is an enlarged view of the distal end of the insertion tube of FIG. 8A.

Turning next the FIG. 8A, a second step of implanting the electrode 100 is depicted. Such second step involves the use of an insertion tube 400. More particularly, the ball electrode 120 is loaded under tension at a distal end 420 of the insertion tube 400, with the flexible wire 140 passing through the insertion tube. The diameter of the insertion tube should be similar to the diameter of the ball electrode 120, e.g., 0.4 mm. As seen in FIG. 8B, which shows an enlarged view of the distal end of the insertion tube of FIG. 8A, the distal end 42 of the insertion tube 400 is preferably beveled to match the curvature of the surface of the ball electrode 120. Such beveling advantageously helps secure the ball electrode 120 firmly at the distal end 420 of the insertion tube when tension is placed on the wire 140 exiting from a proximal end 440 of the tube, thereby preventing the ball electrode 120 from rolling off of the distal tip when it is forced through the slit 190 of the round window.

Figure 9A:
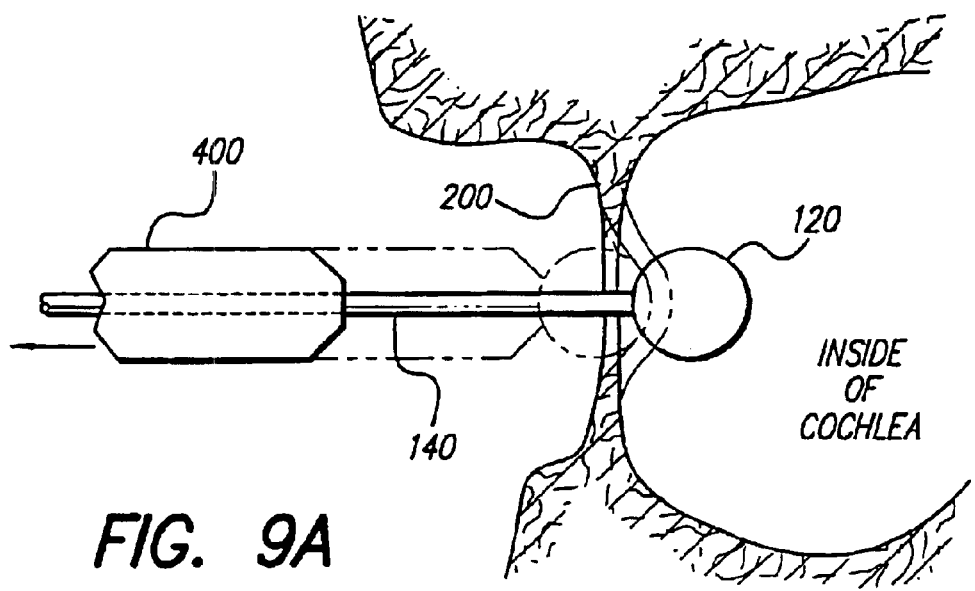
FIG. 9A schematically illustrates the manner in which the ball electrode is pushed through the small insertion so as to reside on the inner side of the round window membrane.
Figure 9B:
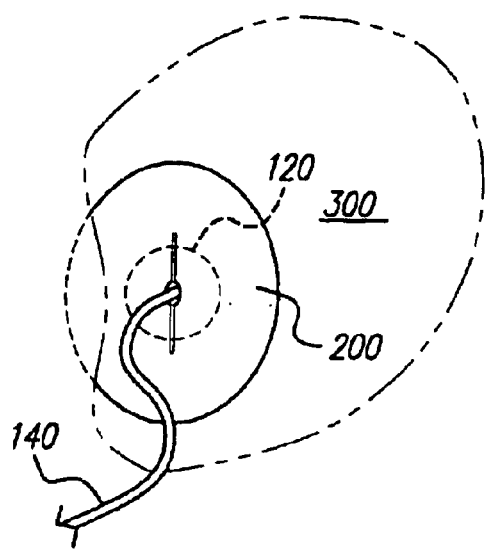
FIG. 9B shows the way in which the round window membrane closes around the thin flexible wire after the ball electrode has been pushed through the slit into the cochlea.

FIG. 9A schematically illustrates a side view of the manner in which the ball electrode 120 is pushed through the small insertion 190 so as to reside on the inner side of the round window membrane 200. FIG. 9B shows a front view of the round window membrane 200 and best illustrates the way in which the round window membrane 200 closes around the thin flexible wire 140 after the ball electrode has been pushed through the slit 190 into the cochlea. Thus, as seen in FIGS. 9A and 9B, the insertion is performed by forcing the ball electrode 120 through the slit 190 while the ball electrode is held under tension at the distal tip 420 of the insertion tube 400. As the ball electrode 120 is forced through the slit 190, the round window membrane 200 will stretch, as needed, to allow the ball electrode to pop through to the inner side, as seen best in FIG. 9A. Once the ball electrode has been thus inserted into the cochlea, the insertion tool 400 may be withdrawn, as shown in FIG. 9A, leaving the round window membrane 200 closed tightly around the thin wire 140, and thereby holding the ball electrode 120 in place and minimizing any leak of fluid from the cochlea.

Figure 10:
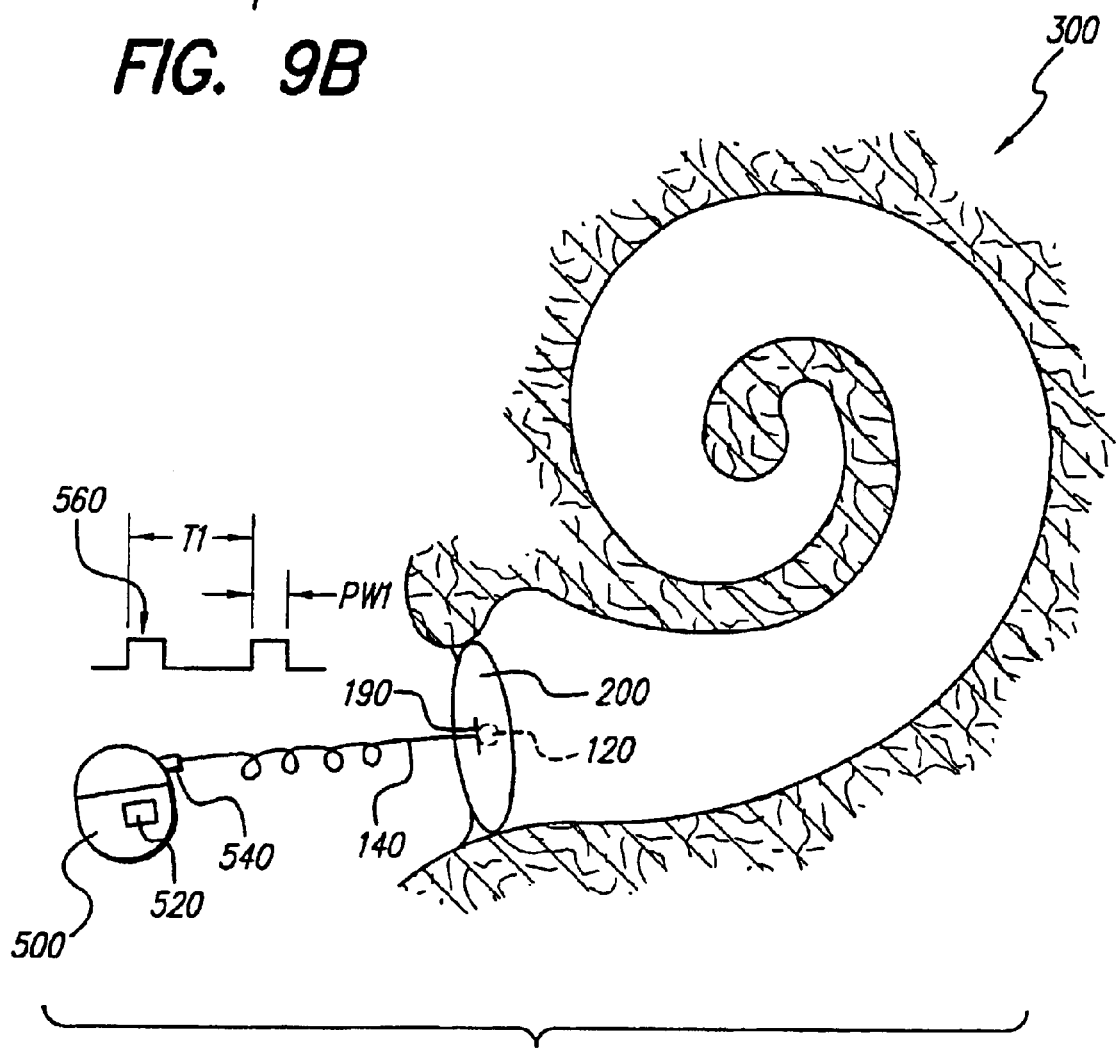
FIG. 10 shows a stimulation or other system that uses the ball electrode of the present invention to, e.g., compensate for high frequency hearing loss, suppress tinnitus, or other purposes.

Once the insertion tube 400 has been removed, the wire 140 may be coiled or otherwise routed to an implanted, or external, electrical circuitry 500, as seen in FIG. 10. For purposes of the following discussion, it is assumed that the electrical circuitry 500 comprises an electrical stimulator, e.g., a pulse generator. However, such circuitry is only exemplary of one type of electrical circuitry that may be used with the invention. The circuitry 500, in addition to comprising a pulse generator, may also comprise monitoring or sensing circuitry, or other types of signal generation circuitry, e.g., an analog current source that can provide continuous or pulsed currents through the electrode ball 120 and a return electrode 520.

The stimulator (or other circuitry) 500 will typically be implanted, but may be external as circumstances warrant. The electrode wire 140 is detachably connected to the circuitry 500 by means of an appropriate connector 540. As an example, the circuitry 500 may generate electrical stimulation pulses 560 which are controlled to occur in a desired spatiotemporal pattern. Here, the term "spatiotemporal" refers to the relative time duration or time delay between pulses of controlled amplitudes. For example, the pulses 560 may comprise a pulse train having a pulse separation time of T1 seconds (thereby providing a pulse repetition rate of 1/T1 Hz), with a pulse width of time PW1, and with a pulse amplitude modulated with an appropriate control signal. The pulse separation time may range, e.g., from 10 microseconds to 100 milliseconds, with a pulse width PW1 ranging from 1 microsecond to 100 milliseconds, depending upon the purpose for which the pulses are applied.

The pulses 560 are applied to the ball electrode 120, which electrode is paired with a suitable reference or return electrode 520. Typically, the return electrode 520 forms an integral part of the case within which the stimulator 500 is housed. The stimulation pattern of electrical pulses 560 applied through the ball electrode are thus applied monopolarly to the cochlear tissue at the basal end of the cochlea. Alternatively, the return electrode may be positioned at any desired location outside or inside of the cochlea; or a second ball electrode could be inserted through the round window membrane near the first, and electrical stimulation applied bipolarly through the two ball electrodes.

The spatiotemporal pattern of electrical pulses applied through one or more ball electrodes (120) is controlled for the purpose of enhancing or compensating for high frequency hearing loss by stimulating the cochlea in the basal region where the electrode ball(s) 120 is/are positioned. Alternatively, or conjunctively, the spatiotemporal pattern of stimulation may be controlled for the purpose of suppression of tinnitus.

Advantageously, because of the small size of the electrode ball 120, the round window membrane 200 is able to continue to function as a vibrating membrane, thereby allowing the normal residual hearing functions of the cochlea and inner ear to continue to function. Hence, the ball electrode 120 is minimally invasive to the hearing process, is easy to implant or insert, and provides desired benefits (compensation of high frequency hearing loss, and/or suppression of tinnitus).

For purposes of the present invention, the stimulator 500 may be of any suitable design. Representative cochlear stimulators that may be used with the electrode 100 are disclosed, e.g., in U.S. Pat. Nos. 3,752,939; 4,400,590; and/or 5,603,726; each of which is incorporated herein by reference. One-channel pulse generators of any conventional design, e.g., of the type commonly employed in single channel implantable pacemakers, could also be employed.

As described above, it is thus seen that the second embodiment of the present invention provides a small ball electrode that may be inserted into the basal end of the cochlea through a minimally invasive insertion process. Such electrode may thereafter be used to stimulate ganglion cells located near the basal end of the cochlea for the purpose of, e.g., compensating for high frequency hearing loss and/or to suppress tinnitus.

As further described above, it is seen that the second embodiment of the invention provides a method of implanting a ball electrode through the round window membrane of the cochlea that is minimally invasive, thereby avoiding, or at least significantly minimizing, any adverse reaction to the implant, such as tissue or new bone formation that adversely affects residual hearing function in the implanted ear.

While the invention herein disclosed has been described by means of specific embodiments and applications thereof, numerous modifications and variations could be made thereto by those skilled in the art without departing from the scope of the invention set forth in the claims.

What is claimed is:

1. A cochlear electrode array (10) comprising:
   a flexible carrier (12), the flexible carrier having a proximal end, a distal end (13), a length L1 no greater than about 8 mm, and a pancake-shaped cross sectional area having opposing flat surfaces, the flat surfaces having a width W2, and the thickness of the carrier between the flat surfaces being a distance W1, wherein the distance W2 is greater than the distance W1 by at least a factor of two;
   a plurality of spaced-apart electrodes (14) carried on the flexible carrier on one of the flat surfaces thereof, the flat surface carrying the electrodes comprising a medial side of the electrode array;
   a plurality of wire contacts (22) embedded within the flexible carrier, at least one wire contact being connected to each electrode;
   a head (18) formed at the proximal end of the flexible carrier having a cross sectional area greater than the cross-sectional area of the flexible carrier, whereby a shoulder (19) is formed at the transition from the flexible carrier to the head;
   a plurality of flexible members (16) attached to the flexible carrier near its proximal end and slopping towards the head;
   wherein the plurality of wire contacts pass through the head and comprise a cable (20) attached to the proximal end of the electrode array, the cable and wire contacts carried therein providing a means for making electrical contact with each of the electrodes.

2. The cochlear electrode array of claim 1 wherein the number of spaced-apart electrodes (14) carried on the medial side of the flexible carrier comprises at least four electrodes and no more than eight electrodes.

3. A method of inserting a cochlear electrode array (10) into a basal region of the scala tympani duct of a human cochlea, the cochlear electrode array having a length no greater than about 8 mm, and further having a pancake-shaped cross-sectional area, the method comprising:
   forming a slit opening (42) into the basal region of the scala tympani duct,
   sliding the cochlear electrode array through the slit; and
   securing a proximal end of the cochlear electrode array inside of the slit, whereby the slit is plugged with the proximal end of the electrode array, thereby preventing fluids from escaping through the slit.

4. The method set forth in claim 3 wherein the step of forming the slit comprises forming a slit in the round window membrane (40) of the cochlea.

5. The method set forth in claim 4 wherein the step of forming the slit in the round window membrane further comprises orienting the slit so that its long side faces a modiolar wall (32) of the cochlea.

6. The method set forth in claim 3 wherein the step of forming the slit comprises first forming a cavity (44) in the bony structure near the basal end of the scala tympani duct, and then forming a slit in the bottom of the cavity, the slit opening into the basal region of the scala tympani duct.

7. A method of using a cochlear electrode (100) to electrically stimulate a human cochlea, the cochlear electrode comprising an insulated flexible wire (140) having a distal end and a proximal end with a ball electrode (120) attached to the distal end of the flexible wire, the method comprising the steps of:
   making a small slit (190) in the round window membrane (20) of a human cochlea (30);
   loading the ball electrode (120) under tension onto a distal tip (420) of a tubular insertion tool (400);
   pushing the ball electrode while loaded on the distal tip of the tubular insertion tool through the slit in the round window;
   removing the tubular insertion tool;
   connecting a proximal end of the flexible wire to an electrical stimulator, the electrical stimulator having means for applying an electrical current to tissue near the ball electrode through the wire connected to the ball electrode and a return electrode.

8. The method of claim 7 further including controlling the stimulation pattern of electrical currents applied to the ball electrode to compensate for high frequency hearing loss.

9. The method of claim 7 further including controlling the stimulation pattern of electrical currents applied to the ball electrode to suppress tinnitus.

* * * * *